United States Patent
Becker et al.

(10) Patent No.: US 6,262,317 B1
(45) Date of Patent: Jul. 17, 2001

(54) PROCESS FOR PREPARING 1,4-BUTANEDIOL BY CATALYTIC HYDROGENATION OF 1,4-BUTINEDIOL

(75) Inventors: Rainer Becker, Bad Dürkheim; Franz Josef Bröcker, Ludwigshafen; Gerd Kaibel, Lampertheim; Rolf Pinkos, Bad Dürkheim; Joachim Wulff-Döring, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/284,209
(22) PCT Filed: Sep. 23, 1997
(86) PCT No.: PCT/EP97/05205
§ 371 Date: Apr. 9, 1999
§ 102(e) Date: Apr. 9, 1999
(87) PCT Pub. No.: WO98/15513
PCT Pub. Date: Apr. 16, 1998

(30) Foreign Application Priority Data

Oct. 10, 1996 (DE) .............................. 196 41 707

(51) Int. Cl.[7] .................................................. C07C 27/00
(52) U.S. Cl. ............................................................ 568/861
(58) Field of Search ............................................. 568/861

(56) References Cited

U.S. PATENT DOCUMENTS

| | | | |
|---|---|---|---|
| 3,847,989 | * 11/1974 | Platz | ...................................... 568/861 |
| 4,153,578 | 5/1979 | DeThomas et al. . | |
| 4,288,640 | 9/1981 | Schuster et al. . | |
| 5,068,468 | 11/1991 | Schossig et al. . | |

FOREIGN PATENT DOCUMENTS

| | | |
|---|---|---|
| 745 225 | 7/1970 | (BE) . |
| 1 941 633 | 3/1971 | (DE) . |
| 2 040 501 | 2/1972 | (DE) . |
| 272 644 | 10/1989 | (DE) . |
| 177 912 | 4/1986 | (EP) . |
| 295 435 | 12/1988 | (EP) . |
| 319 208 | 6/1989 | (EP) . |
| 1 242 358 | 8/1971 | (GB) . |
| 1 362 071 | 7/1974 | (GB) . |
| 202 913 | 12/1967 | (RU) . |

* cited by examiner

Primary Examiner—Michael L. Shippen
(74) Attorney, Agent, or Firm—Keil & Weinkauf

(57) ABSTRACT

A process for preparing 1,4-butanediol by continuous catalytic hydrogenation of 1,4-butynediol comprises reacting 1,4-butynediol with hydrogen in the liquid continuous phase in the presence of a heterogeneous hydrogenation catalyst at from 20 to 300° C., a pressure of from 1 to 200 bar and values of the liquid-side volumetric mass transfer coefficient $k_L a$ of from $0.1\ s^{-1}$ to $1\ s^{-1}$ a) using a catalyst suspended in the reaction medium, where if a packed bubble column is employed this is operated in the upflow mode and at a ratio of gas leaving the reaction vessel to gas fed to the reaction vessel of from 0.99:1 to 0.4:1, or b) passing the liquid and gas in cocurrent in an upward direction through a fixed-bed reactor operated in the gas-circulation mode while maintaining a ratio of the gas fed to the reaction vessel to gas leaving the reaction vessel of from 0.99:1 to 0.4:1.

8 Claims, 4 Drawing Sheets

Figure 1:
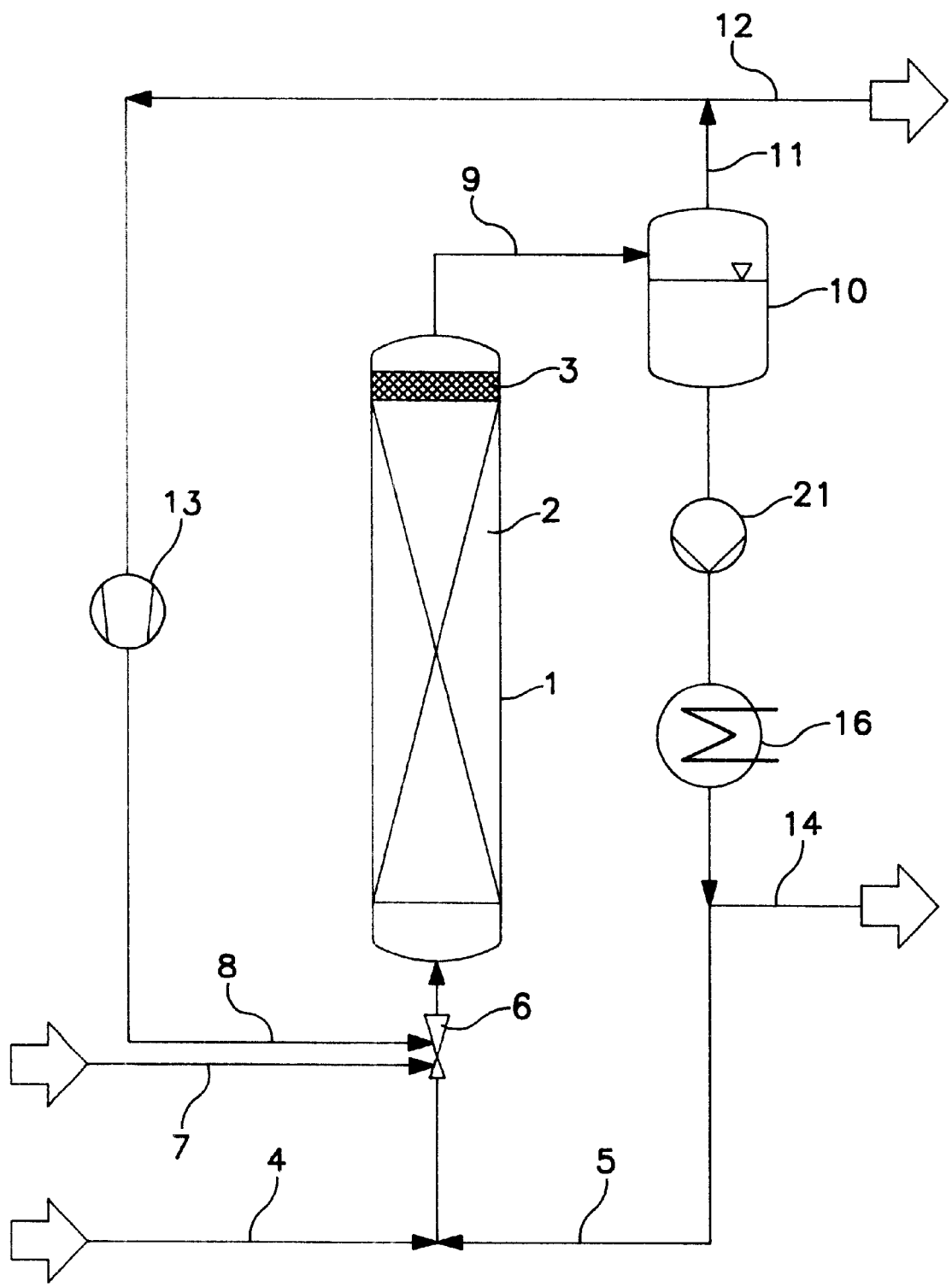

PROCESS FOR PREPARING 1,4-BUTANEDIOL BY CATALYTIC HYDROGENATION OF 1,4-BUTINEDIOL

The present invention relates to a process for preparing 1,4-butanediol by catalytic hydrogenation of 1,4-butynediol with hydrogen in the presence of a solid hydrogenation catalyst at a pressure of from 1 to 200 bar and values of the volumetric liquid-side mass transfer coefficient $k_L a$ of from 0.1 s$^{-1}$ to 1 s$^{-1}$, where the liquid forms the continuous phase and the hydrogen forms the dispersed phase.

The hydrogenation of 1,4-butynediol to give 1,4-butanediol via the individual steps shown in simplified form in the following scheme

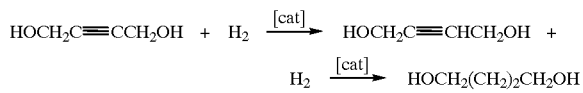

has been carried out for decades and has been described many times. However, the known processes have the disadvantages of a low, uneconomical space-time yield (STY), ie. the amount of starting material used per reactor volume and unit time, when hydrogenation is carried out at pressures below 200 bar, low catalyst lives and low selectivity. In addition, when fixed-bed catalysts are used, the hydrogenation requires a high pressure of over 200 bar which is associated with high capital costs.

Furthermore, 1,4-butynediol, 1,4-butenediol and compounds derived therefrom, eg. the acetal from butanediol and hydroxybutyraldehyde which is formed by isomerization of butenediol, can be separated by distillation from 1,4-butanediol only with difficulty, if at all. However, for the further processing of 1,4-butanediol, it is critical for most applications that no incompletely hydrogenated products are present therein.

In chemical reactions, the selectivity generally decreases with increasing conversions. Efforts are therefore made to carry out the reaction, on the one hand, at as low as possible a temperature and, on the other hand, with a partial conversion in order to obtain selectivities which are as high as possible. In the hydrogenation of butynediol, complete conversion is essential with regard to the product quality achievable on work-up and the hydrogenation is therefore often distributed over a plurality of reactors which are operated under different conditions.

U.S. Pat. No. 5,068,468 discloses the hydrogenation of 1,4-butynediol over solid supported nickel/copper catalysts in which space-time yields of 0.3 kg of butanediol/l·h at a pressure of 250 bar.

BE-B 745 225 describes the use of fixed-bed Raney nickel catalysts at 259 bar, which achieve a space-time yield of 0.286 kg of butanediol/l·h in a two-stage process.

U.S. Pat. No. 4,153,578 discloses a two-stage process for the hydrogenation of 1,4-butynediol over suspended Raney nickel/molybdenum catalysts at a pressure of 21 bar. This process achieves space-time yields of 0.06 kg of butanediol/l·h.

DD-A 272 644 describes the suspension hydrogenation of aqueous butynediol over nickel/SiO$_2$ catalysts. Assuming that butynediol is as usual used in a concentration of from 39 to 50% by weight and assuming complete conversion, the space-time yield is calculated as from 0.15 to 0.25 kg of butanediol/l·h at a pressure of 15 bar. The catalyst used displays a loss in activity of 37% after only 50 hours.

For Example 1 of U.S. Pat. No. 2,967,893, a space-time yield of about 0.01 kg of butanediol/l·h can be calculated for the Raney nickel-copper-catalyzed hydrogenation of 1,4-butynediol.

RU-A 202 913 describes the hydrogenation of butynediol over a nickel/chromium catalyst at a space-time yield of 0.1 kg of butanediol/l·h.

EP-B 0 319 208, DE-A 19 41 633 and DE-A 20 40 501 disclose, inter alia, general hydrogenation processes which can be applied to 1,4-butynediol and in which the gas-circulation operating mode of the reactor is avoided by gas and liquid phases flowing in cocurrent from the bottom upwards through a fixed-bed catalyst. Here, gas and liquid phases flow through the catalyst in the form of the transition stream, with the liquid phase forming the continuous phase.

However, these processes have the disadvantage that in the case of high butynediol loadings in the hydrogenation feed the reaction mixture at the end of the reaction zone is depleted in hydrogen and as a result only an incomplete conversion of the 1,4-butynediol is achieved, thus leading to intermediates which can be separated from butanediol only with difficulty, if at all.

In the case of lower butynediol loadings, a complete conversion and satisfactory product quality can be achieved only if a significantly reduced space-time yield or higher operating pressure is accepted.

It is an object of the present invention to provide a process for the catalytic hydrogenation of 1,4-butynediol to 1,4-butanediol by means of which a high space-time yield together with high selectivity and high catalyst operating lives can be achieved at a pressure of below 200 bar even when using technical-grade 1, 4-butynediol.

We have found that this object is achieved by a process for preparing 1,4-butanediol by continuous catalytic hydrogenation of 1,4-butynediol, which comprises reacting 1,4-butynediol with hydrogen in the liquid continuous phase in the presence of a hydrogenation catalyst at from 20 to 300° C., preferably from 60 to 220° C. and particularly preferably from 120 to 180° C., a pressure of from 1 to 200 bar, preferably from 3 to 150 bar and particularly preferably from 5 to 100 bar, and values of the liquid-side volumetric mass transfer coefficient $k_L a$ of from 0.1 s$^{-1}$ to 1 s$^{-1}$, preferably from 0. 2 s$^{-1}$ to 1 s$^{-1}$, a) using a catalyst suspended in the reaction medium, where if a packed bubble column is employed this is operated in the upflow mode and at a ratio of gas leaving the reaction vessel to gas fed to the reaction vessel of from 0.99:1 to 0.4:1, or b) passing the liquid and gas in cocurrent in an upward direction through a fixed-bed reactor operated in the gas-circulation mode while maintaining a ratio of the gas fed to the reaction vessel to gas leaving the reaction vessel of from 0.99:1 to 0.4:1.

The process of the present invention gives 1,4-butanediol in high space-time yields together with high selectivity at a pressure below 200 bar by means of a single-stage or multistage hydrogenation. In addition, long catalyst operating lives can be achieved.

The liquid-side volumetric mass transfer coefficient between the gas phase and the liquid phase $k_L a$ is defined as $$k_L a = k_{GL} \times F_{GL},$$

where $k_{GL}$ is the mass transfer coefficient for gas-liquid mass transfer and $F_{GL}$ is the gas-liquid phase boundary area. The $k_L a$ value is, for example in Ullmanns Encyclopädie der technischen Chemie, Verlag Chemie, 4th edition (1973), Volume 3, pages 495 to 499, also described as the specific absorption rate.

The $k_L a$ value is determined experimentally by measuring the hydrogen absorption of a mixture of 50% by weight of butanediol and 50% by weight of water at the intended operating temperature. The procedure for the experimental determination of $k_La$ has been described many times in the specialist literature, for example in P. Wilkinson et al.: "Mass Transfer and Bubble Size Distribution in a Bubble Column under Pressure", Chemical Engineering Science, Vol. 49 (1994) No. 9, pp. 1417–1427, Ullmanns Encyclopadie der technischen Chemie, Verlag Chemie, Weinheim/Bergstr., 4th edition, 1973, Volume 3, pp. 495–499, H. Hoffmann: "Gepackte Aufstrom-Blasensaulen", Chem.-Ing.-Tech. 54, (1982) No. 10, pp. 865–876 and A. Marquez et al.: "A Review of Recent Chemical Techniques for the Determination of the Volumetric Mass-transfer Coefficient $k_La$ in Gas-liquid Reactors", Chemical Engineering and Processing, 33 (1994) pp. 247–260.

According to the high $k_La$ values which are employed in carrying out the process of the present invention, it is preferable to measure the hydrogen absorption under continuous operating conditions. As large as possible a stream of the liquid mixture is fed in, hydrogen-free and if appropriate together with suspended catalyst, at the desired temperature. The flow of the liquid mixture should be sufficiently high for the liquid contents of the reactor to be replaced at least within 2 minutes, preferably within 1 minute or less. At the same time, hydrogen-laden liquid mixture is taken off, depressurized to atmospheric pressure and the dissolved hydrogen thus liberated is determined volumetrically. The partial pressure of hydrogen in the gas phase is likewise measured.

The process of the present invention is preferably carried out using technical-grade 1,4-butynediol which is in the form of an aqueous solution and can additionally contain, as insoluble or dissolved constituents, components from the butynediol synthesis, eg. copper, bismuth, aluminum or silicon compounds. of course, it is also possible to use butynediol which has been purified, eg. by distillation. Butynediol can be produced industrially from acetylene and aqueous formaldehyde and is customarily hydrogenated as a 30–60% strength by weight aqueous solution. However, hydrogenation can also be carried out in other solvents, for example alcohols such as methanol, ethanol, propanol, butanol or 1,4-butanediol. The hydrogen required for the hydrogenation is preferably used in pure form, but: it can also contain further components such as methane and carbon monoxide.

According to the present invention, catalysts used are those which are capable of hydrogenating C=C triple and double bonds to single bonds. They generally comprise one or more elements of transition groups I, VI, VII and VIII of the Periodic Table of the Elements, preferably the elements copper, chromium, molybdenum, manganese, rhenium, iron, ruthenium, cobalt, nickel, platinum and palladium. Particular preference is given to catalysts which comprise at least one element selected from among copper, chromium, molybdenum, iron, nickel, platinum and palladium.

The metal content of these catalysts is generally 0.1–100% by weight, preferably 0.2–95% by weight, particularly preferably 0.5–95% by weight.

The catalyst preferably further comprises at least one element selected from among the elements of main groups II, III, IV and VI, transition groups II, III, IV and V of the Periodic Table of the Elements and the lanthanides as promoter to increase the activity.

The promoter content of the catalyst is generally up to 5% by weight, preferably 0.001–5% by weight, particularly preferably 0.01–3% by weight.

As catalysts, it is possible to use precipitation, supported or Raney type catalysts whose preparation is described, for example, in Ullmanns Encyclopädie der technischen Chemie, 4th edition, 1977, Volume 13, pages 558–665.

Support materials which can be used are aluminum oxides, titanium oxides, zirconium dioxide, silicon dioxide, clays such as montmorillonites, silicates such as magnesium or aluminum silicates, zeolites and activated carbons. Preferred support materials are aluminum oxides, titanium dioxides, silicon dioxide, zirconium dioxide and activated carbons. Of course, mixtures of various support materials can also serve as supports for catalysts which can be used in the process of the present invention.

These catalysts can be used either as shaped catalyst bodies, for example as spheres, cylinders, rings and spirals, or in the form of powders.

Suitable Raney type catalysts are, for example, Raney nickel, Raney copper, Raney cobalt, Raney nickel/molybdenum, Raney nickel/copper, Raney nickel/chromium, Raney nickel/chromium/iron or rhenium sponge. Raney nickel/molybdenum catalysts can be prepared, for example, by the method described in U.S. Pat. No. 4,153,578. However, these catalysts are also sold by, for example, Degussa, 63403 Hanau, Germany. For example, a Raney nickel-chromium-iron catalyst is sold under the trade name Katalysator Typ 11 112 W® by Degussa.

When using precipitated or supported catalysts, these are reduced at from 150 to 500° C. in a stream of hydrogen or hydrogen/inert gas at the beginning of the reaction. This reduction can be carried out directly in the synthesis reactor. If the reduction is carried out in a separate reactor, the catalysts can be passivated on the surface at 30° C. using oxygen-containing gas mixtures before being removed from the separate reactor. In this case, the passivated catalysts can be activated at 180° C. in a stream of nitrogen/hydrogen in the synthesis reactor before being used, or can also be used without activation.

The catalysts can be used in a fixed bed or in suspension. If the catalysts are in the form of a fixed bed, the reactor is, according to the present invention, not operated in the customary downflow mode but using an upward cocurrent of liquid and gas in such a way that the liquid and not the gas is present as the continuous phase.

Suspended catalysts are used in a particle size of generally 0.1–500 μm, preferably from 0.5 to 200 μm, particularly preferably from 1 to 100 μm.

If suspended catalysts are employed, then, when using packed bubble columns, the reaction is likewise carried out using an upward cocurrent of liquid and gas in such a way that the liquid and not the gas is present as the continuous phase. The ratio of gas leaving the reaction vessel to gas fed to the reaction vessel is, when using fixed-bed reactors and when using packed bubble columns with a catalyst suspended in the reaction medium, from 0.99:1 to 0.4:1.

The ratio of gas leaving the reaction vessel to gas fed to the reaction vessel which is to be adhered to according to the present invention in the case of fixed-bed reactors and in the case of catalysts suspended in the reaction medium in packed bubble columns can be easily set by either metering in the appropriate amount of hydrogen as fresh gas or, as preferred in industry, recirculating circulation gas and only making up the loss of hydrogen resulting from chemical reaction and waste gas by fresh hydrogen.

The molar ratio of hydrogen to butynediol in the reactor is at least 3:1, preferably from 4:1 to 100:1.

The process of the present invention is carried out over fixed-bed catalysts in a gas-circulation mode, ie. the gas leaving the reactor is circulated, if appropriate after being supplemented with fresh hydrogen, via a compressor back to the reactor. It is possible to convey the total amount of circulation gas or a partial amount thereof via a jet compressor. In this preferred embodiment, the circulation-gas compressor is replaced by an inexpensive nozzle. The work of compression is introduced via the liquid which is likewise circulated. The increase in pressure of the liquid required to operate the jet compressor is from about 3 to 5 bar.

Figure 2:
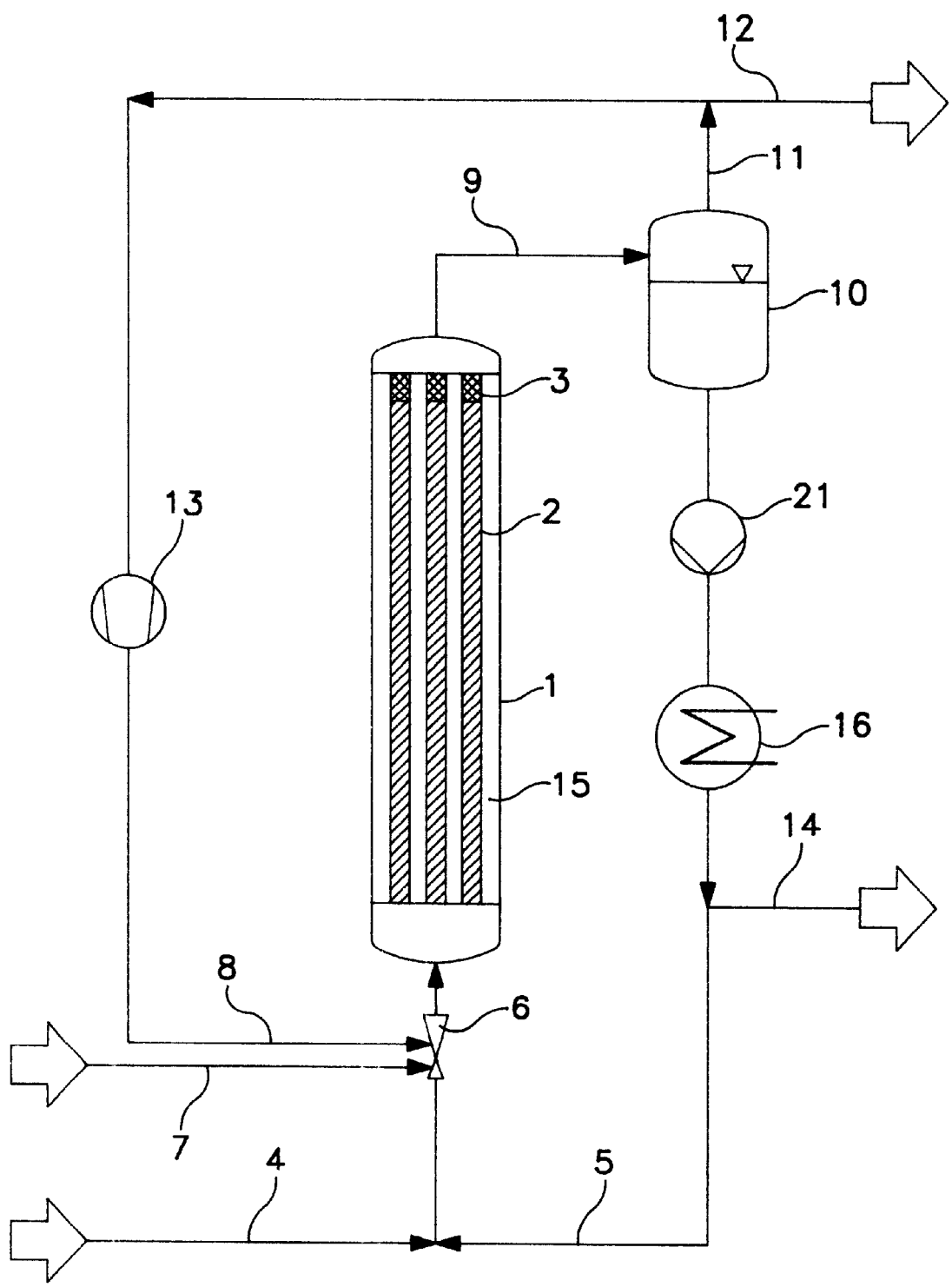

Suitable reactors for carrying out the process of the present invention over fixed-bed catalysts are, for example, the fixed-bed reactor shown in FIG. 1 or a tube-bundle reactor as shown in FIG. 2.

FIG. 1 schematically shows the arrangement of a fixed-bed reactor which can be used in the process of the present invention. The reactor 1 contains a bed of catalyst particles 2 having a mean diameter of from about 1 to 20 mm, preferably from 2 to 5 mm. To prevent the catalyst particles from being carried from the reactor, a wire mesh 3 is located at the upper end of the catalyst bed. The liquid feed 4 comprising butynediol and water is advantageously conveyed via the line together with circulation liquid via line 5 as driving jet to a mixing nozzle 6 in which fresh hydrogen via line 7 and circulation gas via line 8 are mixed in. A two-phase gas/liquid mixture 9 leaves the upper end of the reactor 1 and is separated in a gas/liquid separator 10. A substream 12 of the gas stream 11 is taken off and discarded to avoid accumulation of inert constituents. The circulation gas stream 8 is recirculated via a compressor 13 into the mixing nozzle 6. This compressor may be omitted if the circulation liquid 5 which is conveyed by the pump 21 can be provided at sufficiently high pressure and the mixing nozzle 6 is designed as a jet compressor. A substream 14 of the circulation liquid is taken off as product stream. The heat of reaction liberated is removed in the heat exchanger 16.

The process of the present invention can be carried out not only in the adiabatically operated fixed-bed reactor described in FIG. 1 but also in the isothermally operated tube-bundle reactor described in FIG. 2.

FIG. 2 schematically shows the arrangement of a tube-bundle reactor in which the catalyst particles 2 having a mean diameter of from about 1 to 20 mm, preferably from 2 to 5 mm, are arranged in the tubes 15.

The ratio of circulation liquid 5 to product 14 is, both in the fixed-bed reactor as shown in FIG. 1 and in the tube-bundle reactor as shown in FIG. 2, from 100:1 to 500:1, preferably 200:1. The diameter of the reactor is such that an empty-tube velocity of from 100 to 1000 m/h is established for the liquid. The appropriate empty-tube velocity is determined for each type of catalyst in a laboratory apparatus. It is advisable to set the empty-tube velocity at the maximum velocity permissible with regard to catalyst abrasion. At empty-tube velocities above about 1000 m/h, it has been found that for small catalyst particles there is an additional limitation set by the increasing pressure drop.

Main influencing parameters for fixing the empty-tube velocity are the catalyst dimensions, its form and particle size distribution and its abrasion behavior. A pressure drop figure of from about 0.02 to 0.15 bar/m can, on the basis of experience, be used as a guide. The amount of gas at the reactor outlet is preferably set such that the resulting empty-tube velocity is approximately comparable to the liquid empty-tube velocity. However, it may be up to 90% lower.

For carrying out the process of the present invention using a catalyst suspended in the reaction medium, suitable reactors are jet nozzle reactors, stirred vessels and bubble columns with packing having a packing surface area of at least 500 m$^2$/m$^3$, preferably from 1000 to 2000 m$^2$/m$^3$. Various types of jet nozzle reactors can be employed if they can ensure, by means of a sufficiently high energy input which, on the basis of experience, is above 2 kW/m$^3$, the high mass transfer from the gas phase to the liquid containing the suspended catalyst particles which is essential for the invention. Jet nozzle reactors which are equipped with an impulse exchange tube are particularly suitable. A widely distributed industrial version of a jet nozzle reactor is, for example, the reactor described in EP-A 0 419 419. For energy input values of from 3 to 5 kW/m$^3$, this reactor still makes it possible to separate out the gas phase in simple separators without having to use additional equipment such as foam centrifuges or cyclones.

Figure 3:
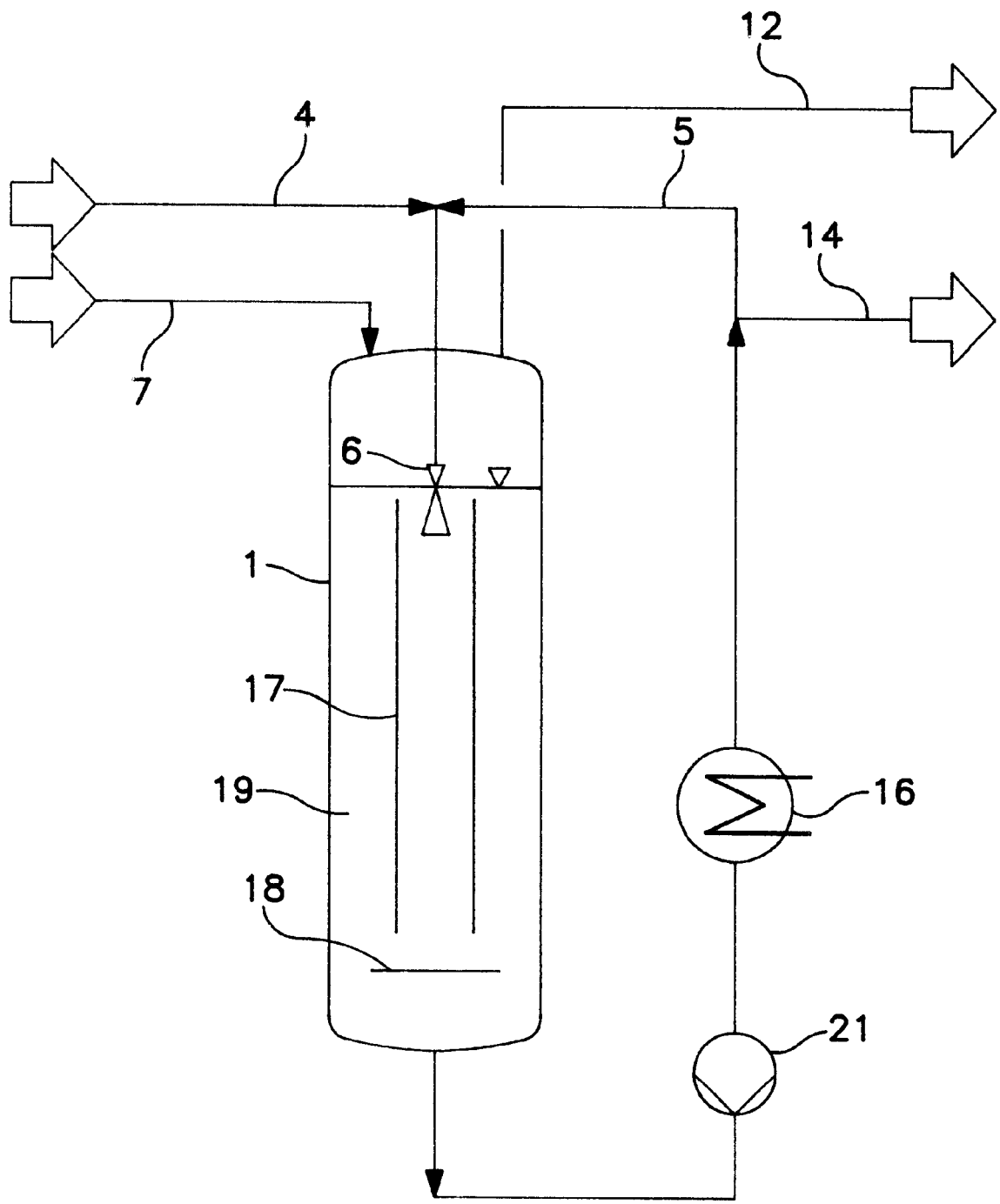

FIG. 3 shows a jet nozzle reactor in which the liquid is conveyed via line 5 via an external circuit having a heat exchanger 16 and draws hydrogen in in a driving jet compressor 6. To intensify the mass transfer, the two-phase mixture is conveyed via an impulse exchange tube 17. At the lower end of the reactor 1, there may be a baffle plate 18 which diverts the flow and makes the separation of the gas easier. The gas rises in the outer annular space 19 toward the top and is again drawn in by the driving jet compressor 6. The liquid from which the gas has been essentially separated is taken off at the lower end of the reactor, conveyed via a heat exchanger 16 to remove the heat of reaction and is again fed to the driving jet compressor 6.

Stirred vessels are suitable for carrying out the process of the present invention only when the energy input is in a range from 2 to 10 kW/m$^3$. To convert the stirrer energy so as to achieve the high $k_L a$ value required by the invention, it is useful for the stirred vessel to have internal fittings which ensure the intimate mixing of gas and liquid, for example baffles.

Figure 4:
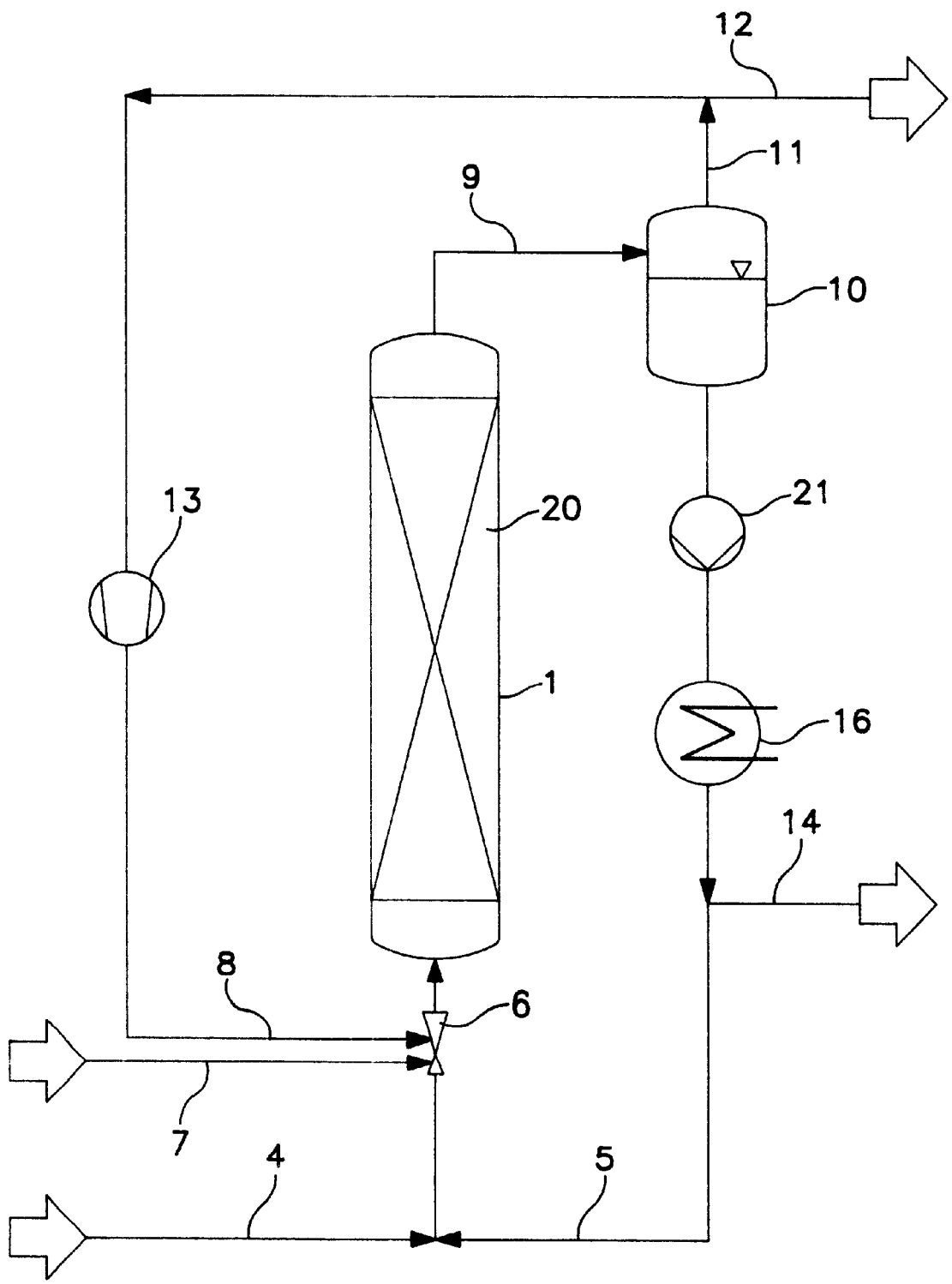

In addition, the bubble columns provided with packing 20 shown in FIG. 4 are also suitable for the process of the present invention. The surface area of the packing has to be at least 500 m$^2$/m$^3$, preferably from 1000 to 2000 m$^2$/m$^3$. The packing 20 can be ordered or random, with ordered packing as is known in terms of its geometry from distillative separation technology having the lowest pressure drop. Packing comprising wire mesh, as is used in similar form in distillation technology, display particularly favorable properties. Examples are the mesh packings Sulzer DX® or Sulzer Ex® which are sold by Sulzer Chemtechn., 8404 Winterthur, Switzerland.

The packing mentioned can also be coated directly with catalytically active components. Such packing is described in EP-A 068 862, EP-A 201 614 and EP-A 448 884. The fixed-bed reactor obtained using one of these packed bubble columns containing such packing has, for similarly high empty-tube velocities for the liquid and the gas of, in each case, from 100 to 1000 m/h, preferably from 200 to 1000 m/h, the same high $k_L a$ values as in the suspension procedure.

The setting of the $k_L a$ values according to the present invention of from 0.1 s$^{-1}$ to 1 s$^{-1}$ which are decisive for simultaneously achieving a high selectivity and a high space-time yield, is carried out by means of targeted technical measures tailored to the respective reactor type. All types of reactor have in common an increased energy input compared with other ways of carrying out such a process. By means of specific structural configurations and operating conditions, the energy introduced is converted very effectively for the improvement of the mass transfer.

When the process of the present invention is carried out using suspended catalysts in stirred vessels, stirrer types having good gas-introducing properties, for example disk stirrers or pitched blade stirrers as are known, for example, from fermentation technology have to be used for setting the $k_L a$ values of from 0.1 s$^{-1}$ to 1 s$^{-1}$. The volumetric energy input is from 2 to 10 kW/m$^3$, with the lower value giving good hydrogenation results only for small apparatuses. In the case of reactor sizes above about 0.5 m$^3$, energy inputs of 5–10 kW/m$^3$ are necessary. In stirred vessels, the energy is introduced via the drive power of the stirrer. These values for the energy input are higher than in the case of customary gas-introduction reactions in stirred vessels, for example fermentations or hydrogenations for which the energy input is from about 0.2 to 1.0 kW/m$^3$.

Jet nozzle reactors with suspended catalysts require volumetric energy inputs of more than 2 kW/m$^3$, preferably 3–5 kW/m$^3$. The energy is introduced by means of the increase in the pressure of the liquid in the circulation pump 21 in combination with the pressure reduction in the driving jet compressor 6. Variation of amount circulated and pressure buildup in the circulation pump enables the desired energy input to be set. The pressure buildup in the pump is usually in the range from 2 to 5 bar.

If catalysts suspended in the reaction medium in packed bubble columns are used in the process of the present invention, the surface area per unit volume of the packings has to be at least 500 m$^2$/m$^3$, but preferably 1000–2000 m$^2$/m$^3$. To set the $k_L a$ values of from 0.1 s$^{-1}$ to 1 s$^{-1}$ which are required for the present invention, simultaneously high liquid and gas velocities of from 100 to 1000 m/h are required. In combination with the indicated geometries of the packing, setting the indicated gas and liquid velocities ensures the necessary energy input which is however, as a result of the type of construction, lower than in the case of stirred vessels or jet nozzle reactors. The achievement of the appropriate energy input which arises from the pressure drop of the flowing liquid and gas can be monitored by measuring the resulting pressure drop which is from 0.02 to 0.15 bar/m of packing. If necessary, the velocity of the liquid can be changed correspondingly in order to set the desired pressure decrease.

The values for the surface area per unit volume, the pressure decrease in the packing and the circulation rates for the liquid and gas given above for the suspension procedure in packed bubble columns also apply to packed bubble columns in which the packing itself is coated with catalytically active material When using fixed-bed reactors in the process of the present invention, the mean size of the catalyst particles has to be 1–20 mm, preferably 2–5 mm, and the velocities of the liquid and gas flowing through have to be 100–1000 m/h to set $k_L a$ values of from 0.1 s$^{-1}$ to 1 s$^{-1}$. The pressure drop established should be about 0.02–0.15 bar/m of fixed bed.

1,4-Butanediol is employed industrially in large amounts, eg. in the preparation of THF or as a diol component in polyesters.

The process of the present invention is illustrated by means of the following Examples. Unless otherwise indicated, use was made of technical-grade butynediol in the form of a 54% strength by weight aqueous solution which contained varying amounts of propynol. The amounts of propynol correspond approximately to the amounts of propanol in the reaction product indicated in the Examples. The percentages in the reaction products in the Examples are, unless otherwise indicated, percentages by weight calculated on an anhydrous basis which have been determined by gas chromatography.

EXAMPLES

Example 1

A stirring autoclave having a liquid level of 130 ml and fitted with two baffles, disk stirrers and built-in level control (a sintered metal frit for holding back the catalyst) was charged with 10 g of Raney Ni/Mo (2% by weight of molybdenum, calculated as Mo, by impregnation of the Raney nickel with ammonium molybdate solution) in 50 ml of water and was subsequently brought to 35 bar with hydrogen. By means of external oil heating, the internal reactor temperature was then brought to 140° C. and a hydrogen flow of 80 standard liters/h was set. The stirrer was set to 700 rpm, which ensured a $k_L a$ of 0.2 s$^{-1}$. 100 g/h of a 54% strength by weight aqueous butynediol solution were then pumped in. The internal reactor temperature rose to 149° C. The reaction product was obtained in an amount of 103 g/h and comprised 94.2% by weight of 1,4-butanediol, 1.3% by weight of n-butanol, 3.3% by weight of n-propanol and a few further products each in an amount of less than 0.08% by weight. The STY was 0.4 kg of butanediol/l·h.

Example 2

Using a method similar to Example 1, 170 g/h of butynediol solution were hydrogenated over 10 g of Raney Ni/Mo (2.5% by weight of molybdenum, calculated as Mo). The initial temperature was 150° C. and the reactor temperature rose to 173° C. during the reaction. The product was obtained in an amount of 176 g/h and comprised 92.4% by weight of 1,4-butanediol, 0.4% by weight of 2-methylbutanediol, 2% by weight of n-butanol and 4.7% by weight of n-propanol plus a few further products in amounts of less than 0.08% by weight. The STY was 0.7 kg of butanediol/l·h.

Example 3

Using a method similar to Example 1, 60 g/h of butynediol solution were hydrogenated over 10 g of Raney Ni/Fe/Cr (type 11 112 W from Degussa). The liquid level in the reactor was 85 ml, the $k_L a$ was 0.2 s$^{-1}$. The initial temperature was 140° C. and then rose to 144° C. The product was obtained in an amount of 64 g/h and comprised 95.7% by weight of butanediol, 0.6% by weight of n-butanol and 1.8% by weight of n-propanol plus a few further products in amounts of less than 0.08% by weight. The STY was 0.25 kg of butanediol/l·h.

Example 4

Using a method similar to Example 1, 60 g/h of butynediol solution were hydrogenated at 600 rpm, corresponding to a $k_L a$ of 0.1 s$^{-1}$, and a reactor temperature of 105° C. The reactor output comprised 90% by weight of butanediol, 1.8% by weight of butenediol, 5% by weight of the acetal of 4-hydroxybutyraldehyde and butanediol, 2% by weight of 4-hydroxybutyraldehyde and 4% by weight of butanol. After increasing the reactor temperature to 136° C., the conversion increased and the following amounts of products were found in the output: 92% by weight of butanediol, 2.7% by weight of the acetal of 4-hydroxybutyraldehyde and butanediol, 0.7% by weight of 4-hydroxybutyraldehyde and 3% by weight of butanol. Example 4 shows that the process of the present invention enables higher selectivities to be achieved at higher conversions.

Example 5

A 400 ml oil-heated tube reactor having a diameter of 2.7 cm was filled with 400 ml of 5 mm diameter Raschig rings made of metal mesh rings of material number 1.4541, steel list issued by Verein Deutscher Eisenhuittenleute, 8th edition, Verlag Stahleisen mbH, Dusseldorf 1990, (UNS-No. S 32100). The tube reactor was installed in a reaction system in which reaction liquid could be circulated via a gas/liquid separator by means of a gear pump. The separator contained a filter through which the liquid and gas could be taken off continuously but which retained the catalyst. The feed of 200 g/h of butynediol as in Example 1 and 100 standard l/h of fresh gas were fed in before the reactor. The reactor was operated in the upflow mode. The space velocity of liquid was 170 m³/m²h, the $k_L a$ was 0.25 s$^{-1}$.

Before the reaction, the reaction system was charged in a similar way to Example 1 with 20 g of Raney Ni/Mo in 300 ml of water. At 30 bar and a reactor temperature of from 145 to 151° C., the product was obtained in an amount of 213 g/h and comprised 93.3% by weight of butanediol, 0.3% by weight of 2-methylbutanediol, 1.5% by weight of n-butanol, 4.2% by weight of n-propanol and a few further products in amounts of less than 0.08% by weight. The STY was about 0.25 kg of butanediol/l·h.

Example 6

The procedure of Example 5 was repeated with 5 g of Raney Ni/Mo being installed. 100 g/h of butynediol solution were hydrogenated at a reactor temperature of about 122° C., 20 bar and 300 l/h of hydrogen. At a space velocity of liquid of 225 m³/m²·h and a $k_L a$ of 0.3 s$^{-1}$ and complete butynediol conversion, n-butanol contents in the product of 2.2–2.7% by weight were obtained, with the 1,4-butanediol content being 77% by weight and the remainder being intermediates. After increasing the space velocity of liquid to 263 m³/m²h, corresponding to a $k_L a$ of 0.4 s$^{-1}$, the n-butanol content fell to 1.3% by weight, the butanediol content rose to 88% by weight.

Example 7

Using a method similar to Example 1, 60 g/h of 57% strength by weight aqueous butynediol solution (water content: 42% by weight) were hydrogenated at a reactor temperature of 127° C. and a $k_L a$ of 0.2 s$^{-1}$. After a reaction time of 125 hours, the product comprised 95.4% by weight of butanediol, 0.1% by weight of 2-methylbutanediol, 1.5% by weight of the acetal of 4-hydoxybutyraldehyde and butanediol, 2.6% by weight of butanol and 0.3% by weight of propanol. The reactor temperature was then increased to 141° C. Subsequently, the conversion of the intermediates also proceeded to completion and the selectivity rose. After an operating time of 173 hours, the following contents were found: 98.8% by weight of butanediol, 0.1% by weight of 2-methylbutanediol, 0.7% by weight of butanol and 0.3% by weight of propanol.

Comparative Example 1

Using a method similar to Example 1, distilled butynediol as a 50% strength by weight aqueous solution was hydrogenated. The pH of the feed solution was adjusted to 6.6 by means of NaOH. At an oil bath temperature of 140° C., an internal reactor temperature of 150° C. was established at a feed rate of 100 g/h. After 24 hours of operation, the reactor output comprised 3% by weight of n-butanol, 0.5% by weight of n-propanol and 96% by weight of 1,4-butanediol. After reducing the stirrer speed to 350 rpm, corresponding to a $k_L a$ of 0.05 s$^{-1}$, the reactor temperature dropped to 141° C. and the reactor output comprised 10% by weight of butynediol, 31% by weight of butenediol, 41% by weight of butanediol, 3% by weight of 4-hydroxybutyraldehyde, 0.5% by weight of propanol plus 4% by weight of butanol and 7% by weight of butenols. The remainder was predominantly acetals.

Comparative Example 2

Using a method similar to Example 1, 100 g/h of technical-grade butynediol solution were reacted at an oil bath temperature of 140° C. using 10 g of Raney Ni/Mo (1.8% by weight of molybdenum, calculated as Mo). The internal reactor temperature was 149° C. The reaction product had the following composition: 94.1% by weight of butanediol, 0.2% by weight of 2-methylbutanediol, 1.5% by weight of butanol and 4.2% by weight of propanol. After reducing the stirrer speed to 350 rpm, corresponding to a $k_L a$ of 0.05 s$^{-1}$, the following hydrogenation result was obtained: 40.3% by weight of butanediol, 37% by weight of butenediol, 2.1% by weight of butynediol, 3% by weight of butanol, 2.6% by weight of butenols, 3.1% by weight of 4-hydroxybutyraldehyde. The remainder to 100% by weight comprised predominantly propanol, propenol and acetals of 4-hydroxybutyraldehyde with the diols.

We claim:

1. A process for preparing 1,4-butanediol by continuous catalytic hydrogenation of 1,4-butynediol in a stirred vessel, which comprises reacting 1,4-butynediol with hydrogen in the liquid continuous phase in the presence of a suspended hydrogenation catalyst at from 20 to 300° C., a pressure of from 1 to 200 bar and values of the liquid-side volumetric mass transfer coefficient $k_L a$ of from 0.1 s$^{-1}$ to 1 s$^{-1}$.

2. A process as claimed in claim 1 carried out at a pressure of from 3 to 150 bar.

3. A process as claimed in claim 1 carried out at a pressure of from 5 to 100 bar.

4. A process as claimed in claim 1, wherein the liquid-side volumetric mass transfer coefficient is from 0.2 s$^{-1}$ to 1 s$^{-1}$.

5. A process as claimed in claim 1, wherein the catalyst used comprises at least one element selected from among the elements of transition groups I, VI, VII and VIII of the Periodic Table of the Elements.

6. A process as claimed in claim 5, wherein the catalyst comprises at least one of the elements copper, chromium, molybdenum, manganese, rhenium, iron, ruthenium, cobalt, nickel, platinum and palladium.

7. A process as claimed in claim 5, wherein the catalyst comprises up to 5% by weight of at least one element selected from among the elements of main groups II, III, IV and VI, transition groups II, III, IV and V of the Periodic Table of the Elements and the lanthanides.

8. A process as claimed in claim 5, wherein the catalyst comprises a support selected from among the oxides of aluminum and titanium, zirconium dioxide, silicon dioxide, clays, silicates, zeolites and activated carbon.

\* \* \* \* \*